United States Patent [19]

Yoon

[11] Patent Number: 5,445,617
[45] Date of Patent: Aug. 29, 1995

[54] AUTOMATIC RETRACTABLE SAFETY PENETRATING INSTRUMENT FOR PORTAL SLEEVE INTRODUCTION AND METHOD OF USE

[76] Inventor: InBae Yoon, 2101 Highland Ridge Dr., Phoenix, Md. 21131

[21] Appl. No.: 848,838

[22] Filed: Mar. 10, 1992

Related U.S. Application Data

[63] Continuation-in-part of Ser. No. 800,507, Nov. 27, 1991, abandoned.

[51] Int. Cl.[6] .................................................. A61M 5/178
[52] U.S. Cl. ..................................... 604/165; 604/158; 604/164; 604/272
[58] Field of Search ............... 604/158, 164, 165, 184, 604/272, 274; 606/185

[56] References Cited

U.S. PATENT DOCUMENTS

| Re. 32,922 | 5/1989 | Levin et al. . |
|---|---|---|
| 1,527,291 | 2/1925 | Zorraquin . |
| 2,496,111 | 1/1950 | Turkel . |
| 2,623,521 | 12/1952 | Shaw . |
| 2,630,803 | 3/1953 | Baran . |
| 4,254,762 | 3/1981 | Yoon . |
| 4,345,589 | 8/1982 | Hiltebrandt . |
| 4,442,836 | 4/1984 | Meinecke et al. . |
| 4,488,545 | 12/1984 | Shen . |
| 4,503,856 | 3/1985 | Cornell et al. . |
| 4,535,773 | 8/1985 | Yoon . |
| 4,559,041 | 12/1985 | Razi . |
| 4,601,710 | 7/1986 | Moll . |
| 4,627,841 | 12/1986 | Dorr . |
| 4,654,030 | 3/1987 | Moll et al. . |
| 4,670,008 | 6/1987 | von Albertini . |
| 4,677,979 | 7/1987 | Burns . |
| 4,747,831 | 5/1988 | Kulli . |
| 4,817,603 | 4/1989 | Turner et al. . |
| 4,820,275 | 4/1989 | Haber et al. . |
| 4,869,717 | 9/1989 | Adair . |
| 4,889,117 | 12/1989 | Stevens . |
| 4,900,307 | 2/1990 | Kulli . |
| 4,902,280 | 2/1990 | Lander . |
| 4,906,236 | 3/1990 | Alberts et al. . |
| 4,931,042 | 6/1990 | Holmes et al. . |
| 4,943,280 | 7/1990 | Lander . |
| 4,946,446 | 8/1990 | Vadher . |
| 4,955,870 | 9/1990 | Ridderheim et al. . |
| 4,966,593 | 10/1990 | Lennox . |
| 4,973,316 | 11/1990 | Dysarz . |
| 4,994,042 | 2/1991 | Vadher . |
| 4,994,068 | 2/1991 | Hufnagle . |
| 5,024,665 | 6/1991 | Kaufman . |
| 5,026,388 | 6/1991 | Ingaiz . |
| 5,030,206 | 7/1991 | Lander . |
| 5,053,016 | 10/1991 | Lander . |
| 5,061,251 | 10/1991 | Juhasz . |
| 5,066,288 | 11/1991 | Deniega et al. . |
| 5,104,382 | 4/1992 | Brinkerhoff et al. . |
| 5,104,383 | 4/1992 | Shichman . |
| 5,114,407 | 5/1992 | Burbank . |
| 5,116,353 | 5/1992 | Green . |
| 5,127,909 | 7/1992 | Shichman . |

(List continued on next page)

FOREIGN PATENT DOCUMENTS

| 2544262 | 4/1977 | Germany . |
|---|---|---|
| 1435246 | 11/1988 | U.S.S.R. . |

*Primary Examiner*—Paul Prebilic

[57] ABSTRACT

An automatic retractable safety penetrating instrument for introducing a portal sleeve into an anatomical cavity via a penetrating member disposed in the portal sleeve includes an operating member biased to move distally upon entry of the instrument into the anatomical cavity to automatically retract the penetrating member into the portal sleeve. The operating member can be carried by the penetrating member to be movable therewith or by a probe movable independent of the penetrating member. The instrument incorporates various locking and releasing mechanisms and spring arrangements chosen dependent upon ease of manufacture and assembly and procedures to be performed with the instrument. The instrument has the appearance of a standard trocar-like penetrating instrument and can be used in a manner familiar to surgeons while producing safety retraction upon entry into an anatomical cavity.

56 Claims, 3 Drawing Sheets

U.S. PATENT DOCUMENTS 5,152,754 10/1992 Plyley et al. .
5,158,552 10/1992 Borgia et al. .
5,207,647 5/1993 Phelps .
5,290,243 3/1994 Chodorow et al. .
5,290,304 3/1994 Storace .
5,295,993 3/1994 Green .
5,312,354 5/1994 Allen et al. .
5,318,580 6/1994 Gresl, Jr. .
5,318,585 6/1994 Guy et al. .
5,320,610 6/1994 Yoon .
5,324,268 6/1994 Yoon .
5,342,382 8/1994 Brinkerhoff et al. .

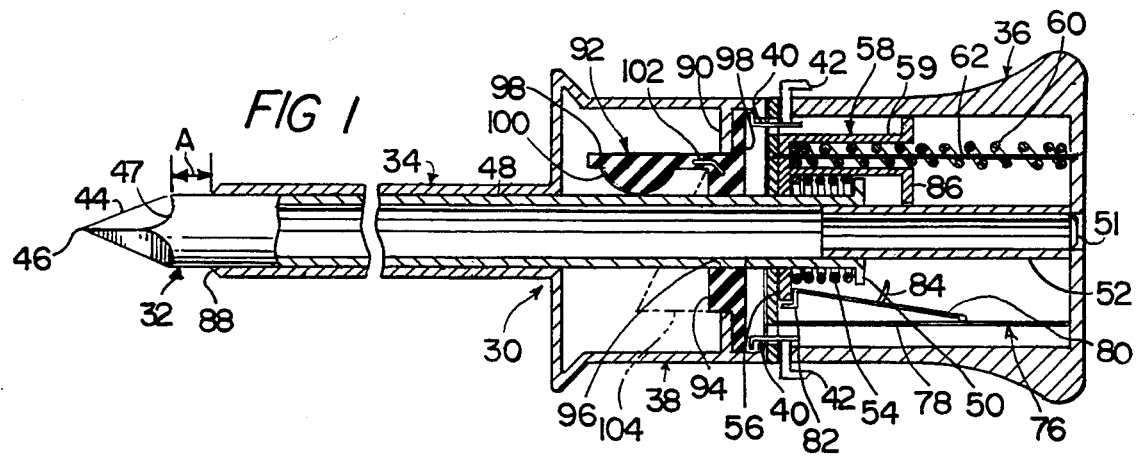
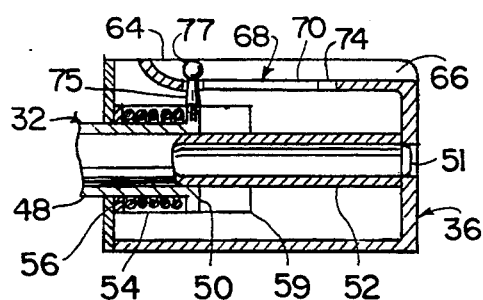
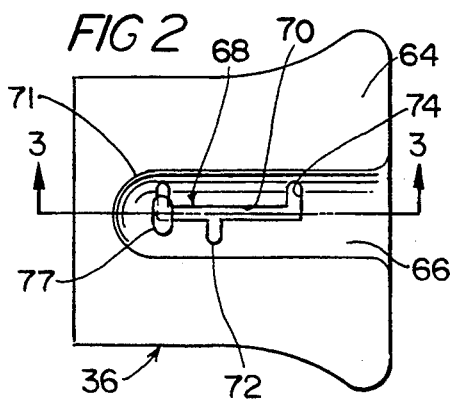
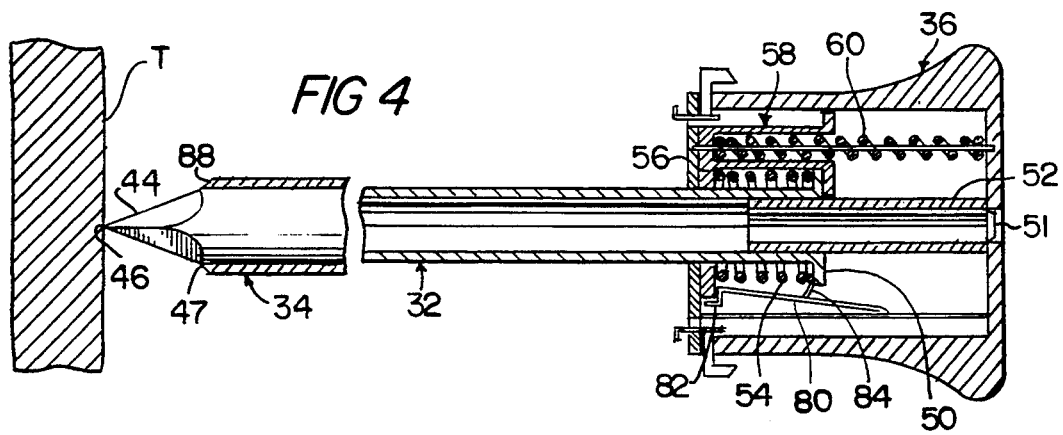
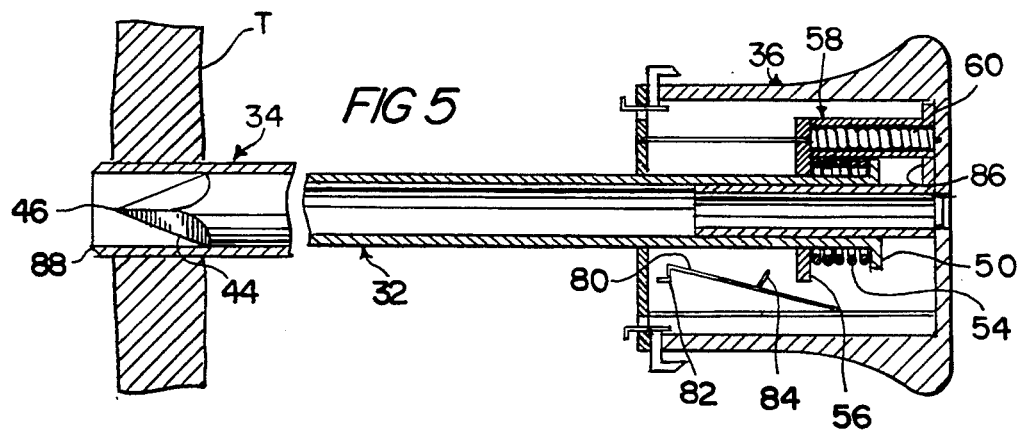

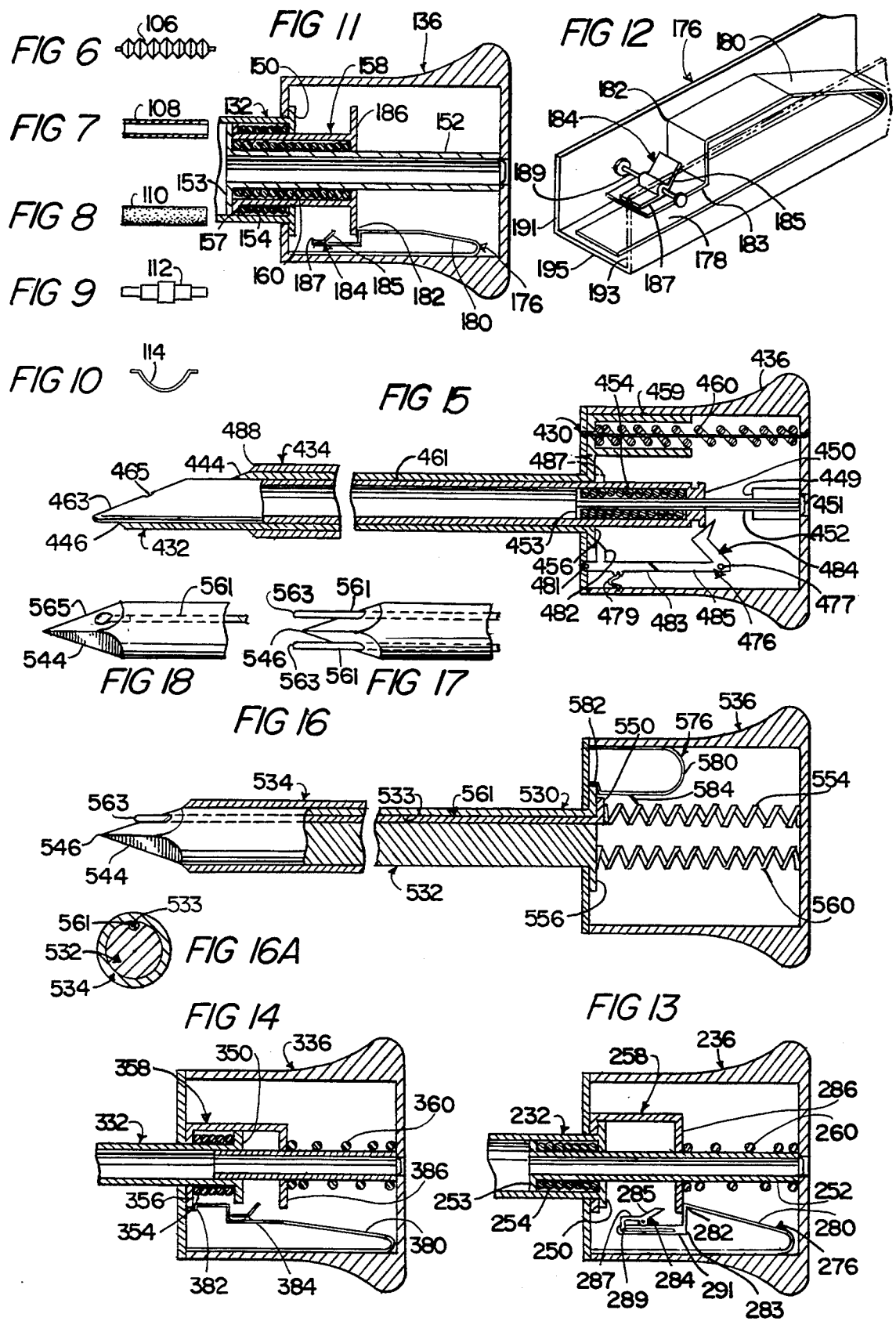

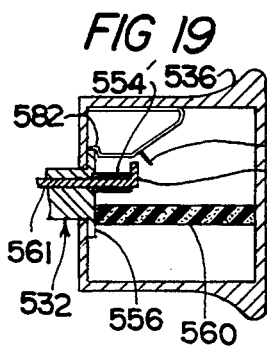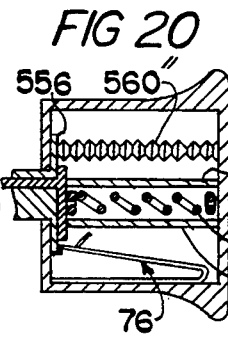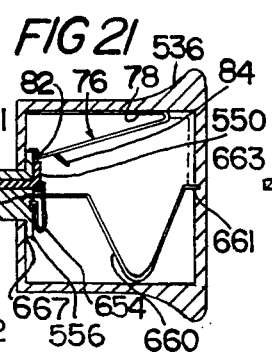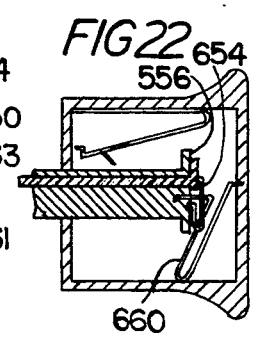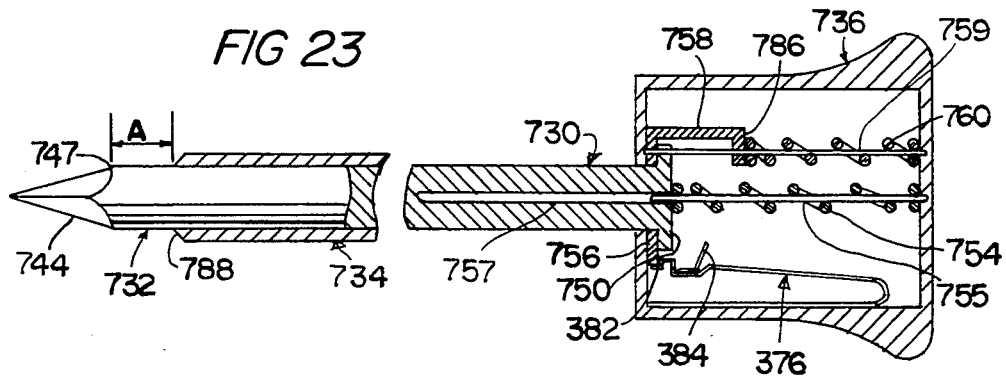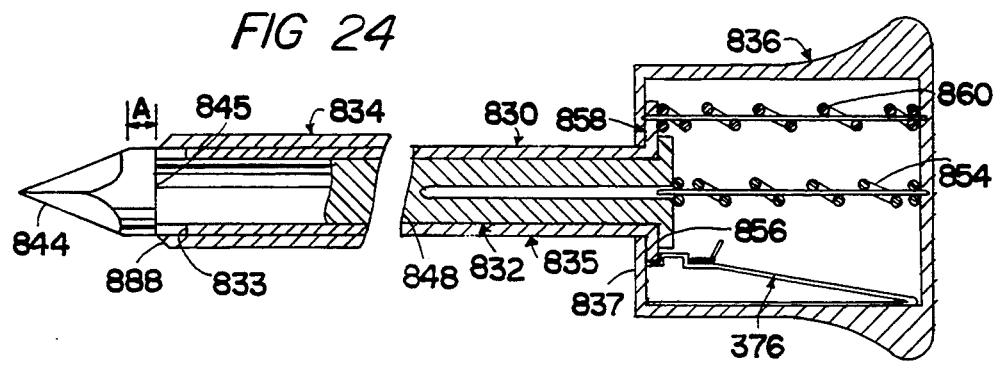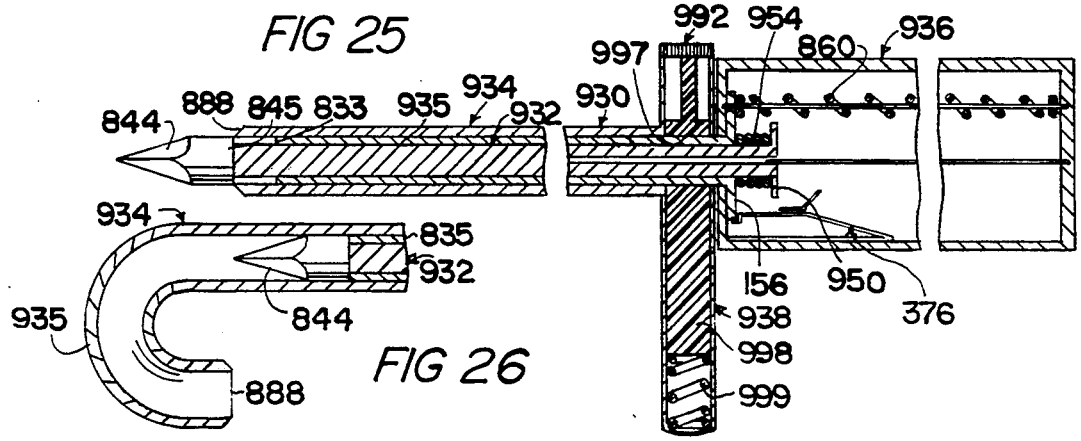

AUTOMATIC RETRACTABLE SAFETY PENETRATING INSTRUMENT FOR PORTAL SLEEVE INTRODUCTION AND METHOD OF USE

CROSS REFERENCE TO RELATED APPLICATION

This application is a continuation-in-part of patent application Ser. No. 07/800,507, filed Nov. 27, 1991, now abandoned, the specification of which is incorporated herein by reference.

BACKGROUND OF THE INVENTION

1. Field of the Invention

The present invention pertains to safety penetrating instruments and, more particularly, to establishing communication with anatomical cavities utilizing automatically retractable safety penetrating instruments having portal sleeves and penetrating members with sharp tips disposed within the portal sleeves for penetrating cavity walls with automatic retraction of the penetrating members into the portal sleeves upon penetration to protect tissue and organ structures within the cavities from the sharp tips of the penetrating members.

2. Discussion of the Prior Art

Penetrating instruments are widely used in medical procedures to gain access to anatomical cavities of various sizes; and, in particular, use of penetrating instruments has become an extremely popular and important first step in endoscopic, or least invasive, procedures to establish an endoscopic portal for many various procedures, with access being established via a portal sleeve positioned during penetration into the cavity with the penetrating instrument. Such penetrating instruments include a penetrating member having a sharp tip or point to pierce or penetrate the tissue forming the cavity wall, and the force required to penetrate the cavity wall is dependent upon the type and thickness of the tissue of the wall. Once the wall is penetrated, it is desirable to protect the sharp tip of the penetrating member to prevent inadvertent contact with or injury to tissue or organ structures in or forming the cavity, and a particular problem exists where substantial force is required to penetrate the cavity wall or the cavity is very small in that, once penetration is achieved, the lack of tissue resistance can result in the sharp tip traveling too far into the cavity and injuring adjacent tissue or organ structures.

Safety trocars having a spring-biased protective shield disposed between an outer sleeve and an inner trocar are marketed by Ethicon, Inc. as the Endopath and by United States Surgical Corp. as the Surgiport. U.S. Pat. Nos. 4,535,773 to Yoon, 4,601,710 to Moll and 4,654,030 to Moll et al are illustrative of such safety trocars. A trocar disposed within a portal sleeve and retractable within the sleeve in response to an electrical signal generated when force from tissue contact is removed from the sharp tip of the trocar is set forth in U.S. Pat. No. 4,535,773 to Yoon.

SUMMARY OF THE INVENTION

It is a primary object of the present invention to provide improved safety penetrating instruments capable of use in a wide variety of procedures and having the general configuration and appearance of standard penetrating instruments.

Another object of the present invention is to provide an automatic retractable safety penetrating instrument in a rest position with a sharp distal tip of a penetrating member in a retracted position within a portal sleeve while a hub coupled with the penetrating member is engaged with a housing coupled with the portal sleeve and to allow the penetrating member to be manually moved to an operative extended position with the sharp distal tip extending beyond the distal end of the portal sleeve.

A further object of the present invention is to provide an automatic retractable safety penetrating instrument in a rest state with bias devices therein disposed in relaxed or unloaded states and moved to biased or loaded states prior to penetration of tissue.

Another object of the present invention is to automatically retract a penetrating member of a safety penetrating instrument to a protected position in response to distal movement of the safety penetrating instrument after a distal end of a portal sleeve enters a body cavity.

A further object of the present invention is to arrange an operating member in a safety penetrating instrument such that movement of the operating member distally places the penetrating member in a protected, safe position within the instrument.

The present invention has an additional object of allowing safe introduction of portal sleeves into body cavities of very small size, such as spinal canal, synovial, pleural or pericardial cavities, for example, by automatically retracting a sharp tip of a safety penetrating instrument within the portal sleeve after the cavity is penetrated thereby minimizing the extension of the safety penetrating instrument into the cavity.

An additional object of the present invention is to provide a method of safely penetrating various anatomical cavities by automatically retracting a penetrating member upon entry into a cavity in response to distal movement of a component of a safety penetrating instrument.

A further object of the present invention is to provide a safety penetrating instrument including a portal sleeve and a distally biased penetrating member disposed within the portal sleeve and having a sharp tip retractable within the portal sleeve in response to movement of the penetrating member due to the distal bias upon penetration through tissue of a cavity wall.

Some of the advantages of the present invention over the prior art are that the automatic retractable safety penetrating instrument can be provided and stored in a rest state with the sharp distal tip withdrawn into the portal sleeve in a safe, protected position and with the bias devices in relaxed states, small or narrow anatomical cavities can be safely penetrated, portal sleeves can safely be introduced into anatomical cavities of various sizes to expand the use of least invasive procedures in many areas including, for example, the cardiac, brain, vascular, chest, genitourinary system, breast and spinal fields, safe penetration of cavities can be accomplished with no parts of the safety penetrating instrument other than the portal sleeve protruding beyond the sharp tip of the penetrating member as is particularly desirable where organ structures adhere to cavity walls, the automatic retractable safety penetrating instrument encourages the use of a smooth, continuous penetrating motion by the surgeon thereby reducing trauma, tears and irregular surfaces in the tissue of the cavity wall, the automatic retractable safety penetrating instrument can be used to penetrate anatomical cavities of the type containing organ structures that could be injured by contact with even a blunt instrument part such as a safety shield, with the use of a threaded distal tip on a penetrating member, penetration of the narrowest of anatomical cavities can be achieved in a safe manner in view of the gradual advancement of the penetrating member coupled with immediate automatic retraction of the penetrating member upon entry into the cavity, safe penetration is achieved while permitting injection or evacuation of fluids, a single puncture can be used for both insufflation and forming an endoscopic portal thereby simplifying diagnostic and surgical procedures, trauma and damage to tissue is minimized, tissue jamming and trapping is avoided and safety penetrating instruments according to the present invention can be inexpensively manufactured to be reusable or disposable for universal use.

The present invention is generally characterized in a method of establishing a portal communicating with an anatomical cavity for the introduction of instruments utilizing an automatic retractable safety penetrating instrument including a portal sleeve and a penetrating member disposed in the portal sleeve including the steps of forcing the automatic retractable safety penetrating instrument through tissue to enter the anatomical cavity with the penetrating member in an extended position wherein a sharp distal tip of the penetrating member extends beyond a distal end of the portal sleeve, biasing an operating member in the automatic retractable safety penetrating instrument to move distally upon entry of the automatic retractable safety penetrating instrument into the anatomical cavity, and automatically retracting the penetrating member in response to distal movement of the operating member to a retracted position wherein the sharp distal tip of the penetrating member is within the portal sleeve. The present invention is further generally characterized in a method of establishing a portal communicating with an anatomical cavity for the introduction of instruments utilizing an automatic retractable safety penetrating instrument including a portal sleeve and a penetrating member disposed in the portal sleeve wherein the automatic retractable safety penetrating instrument is provided in a rest state where the penetrating member is in a retracted position wherein a sharp distal tip of the penetrating member is within the portal sleeve and, for use, the penetrating member is moved from the retracted position to an extended position wherein the sharp distal tip of the penetrating member extends from a distal end of the portal sleeve. The automatic retractable safety penetrating instrument utilizes various arrangements of locking and releasing or trigger mechanisms and bias devices of various types including coiled compression and tension springs, bellows or accordion springs, telescoping springs and springs made of elastic materials such as rubber, sponge, foamed plastic and the like. When the automatic retractable safety penetrating instrument is in the rest state, the springs are preferably in a relaxed, unbiased condition to extend their shelf life; and, when the penetrating member is moved to the operative, extending position, the springs are placed in biased or loaded conditions.

These and other objects and advantages of the present invention will become apparent from the following description of the preferred embodiments taken in conjunction with the accompanying drawings wherein identical reference numbers are used for identical parts and references with one hundred or multiples thereof are used for similar parts.

BRIEF DESCRIPTION OF THE DRAWINGS

FIG. 1 is a broken side view, partly in section, of an automatic retractable safety penetrating instrument according to the present invention.

FIG. 2 is a top view of the hub of the automatic retractable safety penetrating instrument of FIG. 1.

FIG. 3 is a section taken along line 3—3 of FIG. 2.

FIGS. 4 and 5 are broken side views, partly in section, illustrating operation of the automatic retractable safety penetrating instrument of FIG. 1.

FIGS. 6, 7, 8, 9 and 10 show various types of springs useful as bias devices in the automatic retractable safety penetrating instrument of the present invention.

FIG. 11 is a broken sectional view of a modification of a hub arrangement for the automatic retractable safety penetrating instrument of the present invention.

FIG. 12 is a broken perspective view of the locking and releasing mechanism of FIG. 11.

FIGS. 13 and 14 are broken sectional views of modifications of hub arrangements for the automatic retractable safety penetrating instrument of the present invention.

FIG. 15 is a broken sectional view of another embodiment of an automatic retractable safety penetrating instrument according to the present invention.

FIG. 16 is a broken sectional view of a further embodiment of an automatic retractable safety penetrating instrument according to the present invention.

FIG. 16A is a cross-section of a modification of the automatic retractable safety penetrating instrument of FIG. 16.

FIG. 17 is a side view of the distal end of a further modification of the automatic retractable safety penetrating instrument of FIG. 16.

FIG. 18 is a side view of the distal end of another modification of the automatic retractable safety penetrating instrument of FIG. 16.

FIGS. 19 and 20 are broken sections of modified hub arrangements for use with the automatic retractable safety penetrating instrument of FIG. 16.

FIG. 21 is a broken sectional view of another hub arrangement for use with the automatic retractable safety penetrating instrument of FIG. 16.

FIG. 22 is a broken sectional view of the hub arrangement of FIG. 21 in the rest or retracted state.

FIGS. 23, 24 and 25 are broken side views, partly in section, of other embodiments of automatic retractable safety penetrating instruments according to the present invention.

FIG. 26 is a broken view of the distal end of the automatic retractable safety penetrating instrument of FIG. 25 after retraction of the penetrating member.

DESCRIPTION OF THE PREFERRED EMBODIMENTS

An automatic retractable safety penetrating instrument 30 according to the present invention is illustrated in FIG. 1 and includes an elongate penetrating member 32, a portal sleeve 34 concentrically disposed around the penetrating member, a hub 36 mounting penetrating member 32 and a valve housing 38 mounting portal sleeve 34. The hub 36 can be latched to housing 38 with the use of any suitable releasable mechanism, such as detents 40 operated by buttons 42, allowing the hub to be removed from the housing withdrawing the penetrating member from the portal sleeve. Accordingly, the automatic retractable safety penetrating instrument 30 can be considered to be formed of a portal unit and a penetrating unit, the portal unit including portal sleeve 34 and housing 38 and the penetrating unit including penetrating member 32 and hub 36.

Penetrating member 32 is preferably made of a medical grade material, such as stainless steel, and has an outer diameter or size dependent upon the surgical procedure to be performed and the anatomical cavity to be penetrated. The penetrating member 32 has a distal end 44 terminating at a sharp tip 46 for penetrating anatomical tissue. The distal end 44 can have various configurations; and, as shown in FIG. 1, the distal end is formed as a trocar with a pyramidal shape defined by equally spaced end surfaces or facets tapering distally to sharp tip 46 and terminating proximally at scalloped edges or junctions 47 joining the facets to an elongated body 48 which can be cylindrical or have any desirable configuration in cross-section. Body 48 extends proximally from the distal end junction 47 to terminate at an operating member or flange 50 at a proximal end of the penetrating member, the proximal end being disposed in hub 36 with body 48 passing through an aperture in a front wall of the hub. The body 48 can be hollow or tubular along the length of the penetrating member, and an aperture (not shown) can be disposed at the distal end 44 to allow communication entirely through the instrument 30 via a valve 51 carried on the rear wall of hub 36, or the body can be partly hollow or tubular to receive a tube 52 extending distally from the rear wall of the hub and into the hollow proximal end of the penetrating member. A coiled helical operating spring 54 is connected between flange 50 and a retraction plate 56 of a retracting member 58, the plate having an aperture therethrough receiving the proximal end of penetrating member 32 and joining a rail arrangement 59 forming a recess for receiving a coiled, helical retracting spring 60 connected between the rear wall of hub 36 and retraction plate 56. If required, a guide rod 62 can extend from the rear wall of the hub to the front wall of the hub passing through retraction plate 56 to provide a guide to maintain the retracting spring 60 in axial alignment.

Hub 36 can be made of any suitable material to be disposable or reusable and has an external configuration to cooperate with housing 38 to be easily grasped with one hand for use in penetrating tissue. Hub 36 can have any desired configuration in cross-section and is shown in FIG. 3 as being substantially rectangular while having a flared profile as shown in FIGS. 1 and 2. A top wall 64 of the hub has a central recessed channel 66 aligned with the longitudinal axis of the automatic retractable safety penetrating instrument, and a slot 68 is disposed in the channel 66 and is formed of a longitudinal portion 70 aligned with the longitudinal axis of the instrument 30, a distal transverse portion 71, an intermediate transverse portion 72 and a proximal transverse portion 74, as best shown in FIG. 2. A pin 76 is threadedly secured in the periphery of flange 50 and extends through slot 68, as best shown in FIG. 3, the pin having a "T" configuration to terminate at an external knob 77. As previously noted, valve 51, which can be of any conventional design, is provided in the rear wall of the hub in alignment with the lumen of tube 52 to allow passage of fluid entirely through the instrument for additional confirmation of cavity penetration via leakage detection and for irrigation and aspiration when the penetrating member is hollow along its length and provided with an aperture at the distal end to establish fluid communication through the instrument.

A retracting mechanism engages the proximal end of the penetrating member 32 and includes the retracting member 58 and retracting spring 60, and the retracting mechanism is actuated by a locking and releasing or trigger mechanism 76 formed of a latch or locking spring having a substantially flat base 78 secured to a wall of hub 36 with an arm 80 bent inwardly therefrom and extending angularly distally in the direction of the longitudinal axis. A bent locking finger or member 82 is carried on the distal end of arm 80 to engage retracting plate 56 and hold the plate against the front wall of the hub to prevent movement thereof when the locking spring is in its normal position as illustrated in FIG. 1. The trigger mechanism 76 has a releasing or trigger member 84 extending rearwardly or proximally from arm 80 at an angle to allow movement of flange 50 thereby in a proximal direction without causing bending of arm 80. The guide rail 59 terminates proximally at a flange 86 acting as a positive stop or abutment member to limit proximal movement of the penetrating member by abutment with flange 50, and trigger 84 is positioned distally of flange 86 by a distance corresponding to the distal movement desired of flange or operating member 50 prior to automatic retraction, as will be explained in more detail hereinafter. The locking and releasing or trigger mechanism can be mounted at any suitable location on the hub and provided with any required configuration to act as a stop or abutment to prevent proximal movement of the retracting member and to be actuated or released by the distally moving operating member. The locking and releasing mechanism can be made as one piece or multiple pieces dependent upon the hub construction and the operating member utilized to actuate the trigger, flange 50 in the embodiment of FIG. 1. As shown, locking member 82 and trigger 84 are unitarily, integrally formed of a single strip of resilient, spring material such as metal or plastic.

Portal sleeve 34 is preferably made of a substantially cylindrical length of rigid or flexible material, such as stainless steel or other suitable, medically acceptable, plastic or metal material, and can be transparent or opaque. The portal sleeve has a distal end 88 having a configuration to produce a smooth profile with distal end 44 of the penetrating member when the instrument is in an operating state to penetrate tissue, and the portal sleeve has a proximal end mounted in or formed with a front wall of valve housing 38 with a lumen extending between the distal and proximal ends. Housing 38 can be made of any suitable material to be disposable or reusable and has a configuration in cross-section corresponding to the cross-sectional configuration of hub 36 with a flared external profile facilitating grasping during use. A wall 90 extends inwardly from housing 38 at the rear end thereof at a position distally spaced from the rear end of the housing to produce a recess for receiving detents 40, the wall 90 having a central passage for receiving a valve assembly 92. Valve assembly 92 can have any conventional configuration to produce a closed or sealed condition upon removal of the penetrating unit; however, in accordance with the present invention, valve assembly 92 is formed of a unitary, one-piece integral construction of rubber or soft plastic to facilitate sealing to prevent fluid flow through the instrument when the penetrating unit is removed. The valve assembly 92 is formed of a body 94 having a passage 96 therethrough and a proximal flange 98 extending outwardly therefrom to be received in the recess at the rear end of the housing 38. The body 94 has a peripheral configuration to fit snugly within the passage through wall 90, and a valve member 98 extends distally from body 94 and has a normally sealed position with a hemispherical bulging end 100 received in the valve seat formed at the end of passage 96 to produce a normally closed, sealed configuration. To provide assisted bias toward the sealed configuration, a spring member 102 can be embedded within the valve assembly 92 to bias the valve member 98 toward the valve seat 96. While the face of the valve seat is illustrated as being transverse to the longitudinal axis of the automatic retractable safety penetrating instrument 30, the valve seat can be angularly oriented as illustrated in phantom at 104.

In use, the automatic retractable safety penetrating instrument 30 is normally provided in a rest state wherein the distal end 44 of penetrating member 32 is retracted within portal sleeve 34 to be in a safe protected condition, the rest state coinciding with the retracted position for the penetrating member, shown in FIG. 5. In the rest state, retracting spring 60 is in a relaxed, unbiased or unloaded state, and the retraction member 58 is moved proximally until flange 86 abuts the rear wall of the hub 36 carrying with it penetrating member 32, it being noted that operating spring 54 is similarly in an unbiased state in the rest position. Accordingly, with the automatic retractable safety penetrating instrument initially provided in a rest state, no loading of the springs 54 and 60 exists such that the strength of the springs is not weakened and shelf life is increased. With the automatic retractable safety penetrating instrument in the rest state, pin 76 can be rotated to be received in transverse slot portion 74 to be locked in that position to assure that the sharp distal end 44 of the penetrating member remains in a protected position. By forming flange 50 separate from the penetrating member and rotatably mounting flange 50 on the proximal end of the penetrating member, pin 76 can be rotated in slot 68 without rotation of the penetrating member. When it is desired to utilize the instrument 30 to penetrate tissue to introduce the portal sleeve into an anatomical cavity, the knob 77 is grasped and moved distally within longitudinal slot portion 70 to the distal end thereof causing retraction plate 56 to move over arm 80 and finger 82 to be locked in place adjacent the front wall of the hub as shown in FIG. 1. Locking of the retraction plate can be confirmed by feel and sound as the locking member snaps into place and also visually by viewing the position of knob 77 relative to slot 68. With the instrument 30 in the extended condition shown in FIG. 1, the distal end junction 47 of the penetrating member will be spaced from the distal end 88 of the portal sleeve by a distance A which distance is the same as the spacing between flange 50 and stop or abutment member 86.

The instrument can now be utilized to penetrate tissue and enter an anatomical cavity in three manners. In a first manner, pin 76 is rotated into transverse slot portion 71 which allows the instrument to be used as a standard trocar since the penetrating member is prevented from retracting. In a second manner, the hub and housing are grasped by the surgeon and the instrument is forced against tissue T, as shown in FIG. 4, causing penetrating member 32 to move proximally against the bias of operating spring 54 until flange 50 abuts stop member 86 at which time the penetrating member will be in the operative position with the distal end junction 47 of the penetrating member aligned with the distal end 88 of the portal sleeve, as shown in FIG. 4. When the flange or operating member 50 moves proximally, the operating member causes trigger member 84 to deflect proximally such that the flange 50 moves proximally past the trigger member, as shown in FIG. 4, wherein the housing 38 is not shown to simplify understanding of the present invention. While the trigger member 84 is shown in FIG. 4 as being closely adjacent or abutting flange 50, trigger member 84 can be positioned at varying distances from flange 50 to control the amount of distal movement of the operating member required before the penetrating member is retracted. In a third manner of operation, the penetrating member is manually moved to the operative position by grasping knob 77, moving the pin 76 proximally in slot portion 70 and then positioning the pin in transverse slot portion 72 to maintain the penetrating member in the operative position with the distal end junction 47 in alignment with the portal sleeve distal end 88. In either of the second or third manners, after the penetrating member is moved to the operative position, the instrument is forced through the tissue T to enter the anatomical cavity with the sharp distal tip 46 of the penetrating member extending beyond the distal end of the portal sleeve with the distal end of the instrument having the configuration of a standard trocar; and, once the distal end of the instrument has passed through the tissue T, operating spring 54 will move penetrating member 32 distally causing distal movement of operating member 50 to engage trigger member 84 and flex arm 80 downwardly looking at FIG. 4 such that locking member 82 is moved out of abutment with retraction plate 56. Accordingly, retracting spring 60 will automatically move the retracting member 58 and the penetrating member to the retracted position shown in FIG. 5 with the sharp distal tip of the penetrating member within the portal sleeve in a safe protected position. When the third manner of operation is utilized, the surgeon can merely utilize his finger to move the pin 76 out of transverse slot portion 72 once tissue penetration has begun thereby allowing retraction upon entry into the anatomical cavity while in the second manner of operation, the knob will continuously remain in the longitudinal slot portion 70 to produce automatic retraction. If desired, the pin 76 can remain in the transverse portion 72 preventing automatic retraction similar to the first manner of operation described above.

Once the distal end of the instrument has entered into the anatomical cavity and the penetrating member has moved to the retracted position, the portal sleeve will have been introduced into the cavity such that the penetrating unit can be withdrawn from the portal unit. When the penetrating member is withdrawn, the valve member 98 will return to the biased position such that end 100 will engage the valve seat 96 to seal the portal unit from fluid flow therethrough from insufflation pressure. The one-piece construction of valve assembly 92 has the advantages of being inexpensive to manufacture by molding and of being easily replaceable when used with reusable portal units. Additionally, the axial length of passage 96 produces an elongate seal with penetrating member 32 minimizing escape of fluid during cavity penetration; and, if an instrument of a different size than the penetrating member is to be introduced after withdrawal of the penetrating unit, the valve assembly can be easily interchanged to install a valve assembly having a passage 96 of a diameter to seal along the different size instrument.

While coiled springs are shown in the instrument 30 with the retracting spring axially offset from the longitudinal axis of the instrument and the operating spring concentric therewith and surrounding the penetrating member, many different arrangements and types of springs or bias devices can be utilized with the present invention. For example, FIG. 6 illustrates a bellows or accordion-type spring 106, FIG. 7 illustrates an elastic, tubular rubber or plastic spring 108, FIG. 8 illustrates an elastic, solid rubber or sponge-like spring 110, FIG. 9 illustrates a telescoping, pan-spring type spring 112 and FIG. 10 illustrates a leaf-spring 114 made of strip of spring or resilient metal or plastic. Any of these spring or bias devices or other bias devices are useful with the present invention having loaded or biased states in either compression or tension.

A modification of a hub arrangement 136 for use with the automatic retractable safety penetrating instrument of the present invention is illustrated in FIG. 11 wherein a penetrating member 132 terminates at a flange or operating member 150 extending inwardly and outwardly, and a retraction member 158 is concentrically disposed within the open proximal end of the penetrating member 132. The retraction member 158 has a proximal flange 186 forming a stop or abutment member to limit proximal movement of the penetrating member and has a distal flange 157 forming an annular space with flange 150 within which a coiled operating spring 154 is disposed and connected to flanges 150 and 157. A retracting spring 160 is mounted in compression between flange 186 and a flange 153 extending from tube 152. A locking and releasing or trigger mechanism 176 is formed in a modular fashion to facilitate assembly within hub 136, the locking and releasing mechanism 176 including a spring strip having a base 178 curving into an arm 180 which joins a locking finger 182 which terminates at an extending portion 183. A trigger member 184 is formed of a cam having opposing legs 185 and 187, the trigger member 184 being rotatably or pivotally mounted on a pin 189 extending between sidewalls 191 and 193 of a case having a floor 195 to which base 178 is secured. By providing the locking and releasing mechanism as a module, the mechanism can be simply assembled and secured within hub 136, and it will be appreciated that any of the locking and releasing mechanisms described herein can be formed in a modular fashion to facilitate assembly of the automatic retractable safety penetrating instrument.

The operation of the modification of FIG. 11 is similar to that described above with respect to instrument 30 in that retraction member 158 is locked against proximal movement by engagement with locking member 182 with flange 186 while penetrating member 132 can move proximally against the bias of spring 154. Once flange 150 has moved to a position in abutment with stop member 186, the distal end of the penetrating member will be aligned with the distal end of the portal sleeve such that the penetrating member is in the operative position; and, after entry into an anatomical cavity, distal movement of the penetrating member from the tension bias of operating spring 154 will cause the operating member 150 to engage leg 185 of trigger cam 184 pivoting the cam and causing leg 187 to engage portion 183 and flex arm 180 to move locking finger 182 out of abutment with flange 186 thereby allowing retracting spring 160 to move the retraction member 158 and the penetrating member 132 to the retracted position with the sharp distal tip of the penetrating member within the portal sleeve due to the coupling of flange 157 to operating member flange 150 via spring 154. While the operation is similar to that described above relative to instrument 30, it will be appreciated that a concentric arrangement of springs is utilized in the modification of FIG. 11 to allow the hub to have minimal depth and the locking finger is disposed proximally of the trigger.

Another modification of a hub arrangement for use with the instrument of the present invention is illustrated in FIG. 13 wherein the hub arrangement 236 includes a retraction member 258 having a "U" shape in cross-section with a proximal flange and stop member 286 locked in place by locking finger 282 of a locking and releasing mechanism 276. Mechanism 276 is similar to mechanism 176 with the exception that trigger cam 284 has a leg 287 carrying a pin 289 at the end thereof, the pin 289 riding in a slot 291 in extending portion 283 to cause flexing of arm 280 when trigger cam 284 is pivoted or rotated counterclockwise looking at FIG. 13 due to distal movement of the operating member formed by flange 250 on the proximal end of the penetrating member 232 to engage leg 285 of trigger cam 284. Retracting spring 260 is connected to stop member 286 and the rear wall of hub 236 to cause automatic retraction of the penetrating member once locking finger 282 is moved away from the end of abutment member 286. Operating spring 254 is connected between flange 250 and flange 253 on the end of tube 252 such that penetrating member 232 is biased by tension on spring 254 to move distally once the automatic retractable safety penetrating instrument has penetrated into an anatomical cavity. The arrangement of springs 260 and 254 in longitudinal coaxial alignment in hub arrangement 236 permits the hub to have minimal width.

The hub arrangement 336 shown in FIG. 14 is similar to hub arrangement 236 with the exception that locking finger 382 is disposed at the end of the arm 380 similar to locking finger 82 in FIG. 1 while trigger cam 384 is similar to trigger cam 184 shown in FIGS. 11 and 12. Operating spring 354 is connected between flange 350 on the proximal end of the penetrating member 132 and a retraction plate 356 similar to plate 56 in FIG. 1. The operation of hub arrangement 336 is similar to that described with respect to hub arrangement 236 with retracting spring 360 connected to stop member 386 and the hub rear wall to be biased in tension to retract the penetrating member into the portal sleeve.

In the automatic retractable safety penetrating instrument 430 shown in FIG. 15, the valve housing is not illustrated in order to simplify the drawing, and instrument 430 utilizes a cannulated penetrating member 432 having an open, angled distal end 444 terminating at a sharp distal tip 446 and aligned with the distal end 488 of portal sleeve 434. The penetrating member 432 terminates proximally at a flange 456 operating as a retraction plate and joining a rail guide 459 receiving a retracting spring 460 connected to the rear wall of the hub 436 and the retraction member 458 formed by plate 456 and rail 459. Retraction member 458 can be formed as one-piece with penetrating member 432 or can be a separate member fastened thereto in any suitable manner. A probe 461 is slidably received within tubular penetrating member 432 and has a blunt distal end 463 extending beyond sharp distal point 446 in the operating state with an aperture 465 therein to allow communication entirely through the instrument 430 in the manner described above with respect to instrument 30. Probe 461 has a proximal end 450 with a flange-like configuration to form an operating member for actuating retraction, and the probe 461 is biased distally by a coiled spring 454 connected between a flange 453 on the distal end of tube 452 and the proximal end of the penetrating member. The locking and releasing or trigger mechanism 476 includes a trigger cam 484 and a locking finger 482 having extending legs 485 and 483, respectively, with complementary angled or beveled ends adjacent or abutting one another. Trigger cam 484 is pivotally mounted on hub 436 at a pivot 477 while locking finger 482 is pivotally mounted on hub 436 at a pivot 481 at a position such that locking finger 482 abuts retraction plate 456, the locking finger being biased toward the locking position by a compression leaf spring 479 engaging the hub and the arm 483 to bias the locking finger counterclockwise looking at FIG. 15. In order to penetrate tissue, the blunt end 463 of the probe 461 is placed against the tissue; and, when the instrument 430 is forced through the tissue, the probe 461 moves proximally such that operating member 450 moves past trigger member 484 causing the trigger to pivot clockwise looking at FIG. 15 thereby not moving locking finger 482. An abutment 449 is supported on the hub 436 at a position to abut the proximal end 450 of probe 461 to limit proximal movement of the probe such that probe distal end 463 is aligned with penetrating member distal end 444, and the distal ends 444 and 463 preferably are arranged at the same angle to produce a substantially solid tissue penetrating tip. With the probe moved proximally and the operating member 450 positioned distally of the trigger 484, the tip of the trigger will be received in the annular recess adjacent operating member 450, and the instrument can be forced through the tissue. Once the distal end of the instrument has entered the anatomical cavity, the probe 461 will move distally under the force of operating spring 454 causing operating member 450 to engage trigger 484 and pivot the trigger counterclockwise to in turn pivot locking finger 482 clockwise due to the beveled engagement of arms 485 and 483 against the bias of spring 479 moving the locking finger away from retraction plate 456 and allowing retracting spring 460 to retract the penetrating member to a safe position within portal sleeve 434, the probe remaining in the extended position. If it is desired to retract the probe along with the penetrating member, a protrusion 487 can be provided on probe 461 to be engaged by the retracting plate such that the probe moves proximally along with the penetrating member. Another manner in which the probe can be retracted with the penetrating member is to provide a pin and slot engagement between the probe and the penetrating member.

An automatic retractable safety penetrating instrument 530 without the valve housing is illustrated in FIG. 16 wherein the penetrating member 532 has a solid trocar distal end 544 terminating at a sharp tip 546, and the penetrating member has a passage 533 longitudinally therethrough receiving a probe 561 having a blunt distal end 563 extending through an aperture in one of the facets of the trocar distal end 544 aligned with the passage 533. The probe 561 carries a flange 550 on the proximal end thereof forming an operating member for the retracting mechanism. A retracting spring 560 is connected between the rear wall of hub 536 and the proximal end of penetrating member 532 which carries a flange 556 forming a retraction member held in place by engagement with a locking finger 582 of a locking and releasing or trigger mechanism 576 having a trigger member 584 extending proximally therefrom for engagement by the operating member 550 in a manner similar to that described above. The probe 561 can protrude from the distal end 544 by any distance such that the blunt end 563 can just barely protrude from the facet or lateral cutting edge of the distal end 544 to be disposed proximally of the sharp tip 546 or can extend distally beyond the sharp tip 546 dependent upon the procedure to be performed.

In operation, when the instrument 530 is forced through tissue, the probe 561 will move proximally against the bias of operating spring 554, which is mounted in compression between operating member 550 and the rear wall of hub 536, until the blunt end 563 is flush with the facet of the distal end 544 at which time the operating member 550 will have moved proximally past trigger 584. Upon entry into the anatomical cavity, the spring 554 will move probe 561 distally causing operating member 550 to engage trigger 584 and flex arm 580 of the trigger mechanism such that locking finger 582 is moved out of engagement with retraction member 556. Accordingly, retracting spring 560 will retract the penetrating member along with the probe into the portal sleeve to a safe protected position. If desired, passage 533 can be formed as a groove 533' in the external surface of the penetrating member such that the probe 561 is disposed externally of the penetrating member and the blunt end 563 is disposed at the lateral edge of the distal tip adjacent the portal sleeve distal end as shown in cross-section in FIG. 16A, or the body of the penetrating member can have a diameter less than the diameter of the portal sleeve to allow the probe to be positioned in the space therebetween external of the penetrating member.

FIG. 17 illustrates a modification of automatic retractable safety penetrating instrument 530 wherein two or more probes 561 extend through the facets of the distal end 544 of the penetrating member. The use of a plurality of probes 561 provides added safety for the situation where one of the probes becomes jammed during tissue penetration; and, further, by arranging the probes to extend blunt ends 563 distally beyond sharp point 546, the probes can provide protection for the tip when the probes are in the extended position shown in FIG. 17. The probes can be utilized to operate a single locking and releasing mechanism or multiple locking and releasing mechanisms positioned in the hub.

In the modification of FIG. 18, a probe 561 contacts a flexible membrane or window 565 disposed on one of the facets of the distal end 544 of the penetrating member such that no openings are produced in the distal end to avoid trapping of tissue. In use, the flexible membrane will move to a position flush with the facet during tissue penetration and, after entry into a cavity, will bulge distally such that the membrane acts as a sensor to sense reduced pressure on the distal tip of the penetrating member. The probe 561 will act as a detector to detect distal movement of the membrane and actuate the trigger mechanism and retraction of the penetrating member. Various detector mediums could be utilized, such as wire, fluid or electrical components like piezoelectric transducers, to detect movement of the membrane, which acts an operating member, and produce a signal to actuate the retracting mechanism. The trigger mechanism will be responsive to the detector signal and could be, accordingly, mechanical, fluidic or electrical in operation.

A modified hub arrangement for the automatic retractable safety penetrating instrument 530 is shown in FIG. 19 wherein distal bias for probe 561 is provided by a tubular rubber sleeve 554' having a distal end mounted in penetrating member 532 and a proximal end secured to operating member 550 such that the operating spring or bias device formed by 554' is in tension when the probe is moved proximally past trigger 584 of the latch mechanism. The retracting spring 560' is formed by an elastic, solid rubber or sponge member secured to the rear wall of hub 536 and to retraction member 556 so as to be in tension or stretched when in the position shown in FIG. 19. In this manner, the retracting spring or bias device 560' will contract upon locking finger 582 releasing flange 556 to retract the penetrating member.

In the modified hub arrangement of FIG. 20, retracting spring 560" is formed by an accordion-like or bellows bias device connected to retraction member 556 and the hub rear wall to be stretched or in tension when in the position illustrated while coiled operating spring 554 is centered in guide walls 555 extending from the hub wall, the spring 554 being positioned laterally of the longitudinal axis to be received within a channel formed by the walls 555.

Another modified hub arrangement is illustrated in FIG. 21 wherein the retracting spring is formed by a leaf or strip metal spring 660 having ends secured to the retraction member 556 on the proximal end of penetrating member 532 and the rear wall of hub 536, the leaf spring 660 being shown in a loaded, tension position in FIG. 21 and in an unloaded, relaxed position in FIG. 22. The operating spring for probe 561 is formed by a U-shaped leaf spring 654 shown in FIG. 21 in its unloaded, unbiased position with one end secured to the proximal end of penetrating member 532 and a second end secured to operating member 550 on the proximal end of probe 561. The locking and releasing mechanism 76 from FIG. 1 is utilized with the modification of FIG. 21 such that trigger 84 is engaged by operating member 550 after penetration into an anatomical cavity due to the bias from leaf spring 654 which is placed in tension during penetration of tissue by proximal movement of the probe 561. Once the locking finger 82 is moved in response to distal movement of the probe, the retracting spring 660 returns to its normal relaxed or unbiased state as shown in FIG. 22 retracting the penetrating member and the probe within the portal sleeve. The locking and releasing mechanism 76 and the springs 660 and 664 can be made of unitary construction from a single strip of resilient metal or plastic by connecting the base 78 of the locking and releasing mechanism with the proximal end 661 of spring 660 as shown in phantom at 663 and by also connecting the distal end 665 of retracting spring 660 with the end 667 of operating spring 654. By appropriately forming the entire locking and releasing mechanism and retracting and operating springs of a one-piece leaf spring construction, assembly and cost of manufacture can be substantially reduced. When the retracting and operating springs and the locking and releasing mechanism are made from a single resilient strip, the retracting spring 660 can have a serpentine configuration to increase spring power.

Another embodiment of an automatic retractable safety penetrating instrument 730 according to the present invention is illustrated in FIG. 23 without the valve housing, the instrument 730 having a construction to be particularly advantageous for economic and simple assembly and manufacture. The locking and releasing mechanism 376 is similar to that shown in FIG. 14 while the retraction member 758 has a plate 756 engaged by the locking finger 382 and a stop or abutment member 786 spaced from a flange 750 on the proximal end of a solid penetrating member 732, the flange forming the operating member for actuating trigger 384. The space between flange 750 and stop member 786 is equal to the distance A between the distal end junction 747 of the penetrating member and the distal end 788 of the portal sleeve 734 such that, as described above with reference to instrument 30, initial proximal movement of the penetrating member is limited by abutment of flange 750 with stop member 786. A coiled operating spring 754 is mounted in compression between flange 750 and the rear wall of hub 736, and a guide rod 755 extends centrally through the spring 754 to be received in an axial channel 757 formed in the proximal end of the penetrating member. The retracting spring 760 is connected between the stop member 786 of retraction member 758 and the rear wall of the hub 736. The guide rod 755 assures non-cocking and smooth retracting movement of the penetrating member after triggering of the locking and releasing mechanism while a guide rod 759 passing through spring 760 provides similar guiding action for the retraction member and the penetrating member.

Another embodiment of an automatic retractable safety penetrating instrument 830 according to the present invention is illustrated in FIG. 24 without the valve housing and has a hub arrangement 836 similar to hub arrangement 736 in instrument 730 with the exception that retraction member 858 is formed as a single plate 856 with no stop member to limit proximal movement of the penetrating member 832. Instead, a positive stop to limit proximal movement of penetrating member 832 to the operative position is formed by the distal end 833 of a sleeve 835 extending distally from retraction member 858 through the front wall 837 of hub 836. The distal end 833 of sleeve 835 is spaced from the distal end 888 of the portal sleeve 834 by a distance A equal to the distance between the distal end junction 847 of the penetrating member and the distal end 888 of the portal sleeve. The penetrating member 832 has a solid body 848 of a diameter less than the diameter of the distal end junction 847 to form a shoulder 845 at the juncture thereof. In this manner, proximal movement of the penetrating member is limited by abutment of shoulder 845 with sleeve distal end 833; and, thus, the hub arrangement is simplified by not requiring a positive stop therein. Springs 854 and 860 are arranged and operate in the same manner as springs 754 and 760 in instrument 730.

FIG. 25 shows an automatic retractable safety penetrating instrument 930 according to the present invention which differs from instrument 830 in that the hub 936 is elongated to allow retraction of the penetrating member 932 substantially within the portal sleeve 934, the sleeve, preferably, having a slender configuration to facilitate handling of the instrument by a surgeon. Portal sleeve 934 is made of a shape memory material, such as a resilient plastic or a spring metal, and has a curved, hook or "J" shaped, non-linear normal configuration while being substantially linear when penetrating member 932 is received in the lumen thereof. The operating spring 954 is mounted between operating member 950 formed by a flange on the proximal end of the penetrating member and retraction plate 856. The valve housing 938 has an elongate, handle-like configuration, and a "trumpet" valve assembly 992 is utilized to control fluid flow through the housing 938. The trumpet valve assembly includes a valve member 998 biased upwardly by a compression spring 999, and the valve member 998 has an aperture 997 therethrough for accommodating sleeve 935 in sealing relation. The retraction operation of instrument 930 is the same as described above with respect to instrument 830 with the exception that distal bias of the penetrating member is established with tension operating spring 954 rather than with a compression spring. Once penetration is achieved, and retraction plate 956 is released by trigger mechanism 376, penetrating member 932 will be retracted a distance slightly less than the longitudinal dimension of hub 936 such that distal end 844 of the penetrating member is substantially within the portal sleeve 934. With the penetrating member in the retracted position, the portion 935 of the portal sleeve 934 distal of the penetrating member distal end 844 will automatically return to the normal predetermined, non-linear configuration, as shown in FIG. 26, where the distal portion extends away from the longitudinal axis of the portal sleeve. The hook or "J" shaped configuration of the portal sleeve distal portion anchors or stabilizes the instrument in the cavity such that the penetrating unit formed of hub 936, penetrating member 932 and sleeve 935 can be withdrawn from housing 938 while the portal unit is securely held in position. After withdrawal of the penetrating unit, spring 999 forces valve member 998 upwardly to seal the housing to prevent fluid flow therethrough. The configuration of valve housing 938 provides a grip-like handle particularly advantageous for certain procedures whether used with the previously described hub configurations or the elongate hub 936.

Automatic retractable safety penetrating instruments according to the present invention can incorporate various features of the modifications and embodiments disclosed herein dependent upon specific procedures to be performed. For example, the penetrating member can be solid or hollow and have distal ends of various configurations, such as trocar or pyramidal, conical, threaded or open needle-like configurations. The positions of the retracting and operating springs can be coaxial, concentric, laterally offset, within the penetrating member or external of the penetrating member dependent upon size constraints for the hub associated with specific uses for the instruments. Where the springs are laterally offset, the hub can have a reduced length; and, where the springs are aligned with the longitudinal axis of the instrument, the hub can have a reduced width. When the springs are concentrically disposed and positioned within the penetrating member, the overall size of the hub is minimized. The springs can be loaded or biased in either tension or compression; and, preferably, the instruments are provided for use with the springs in a relaxed or unloaded state to increase shelf life. The pin and slot arrangement between the penetrating member and the hub provides the surgeon with control over the instrument to allow use without retraction and to allow manual movement of the penetrating member to an operative position with the distal end of the penetrating member extending from the distal end of the portal sleeve and in alignment therewith to have the appearance of a standard trocar penetrating instrument. By disposing the knob 77 in a recessed channel, accidental dislodging of the pin 76 in the slot 68 is prevented. Movement of the pin also produces a visual indication of retracting and extending operation of the instrument which can also be determined by feel and sound both upon movement to the locked extended position and to the retracted position.

The hub arrangement used in the automatic retractable safety penetrating instruments will depend on procedural requirements and the springs and locking and releasing mechanisms housed therein. Where a fluid passage is desired through the instrument, a guide tube can be used to extend from the hub rear wall into the hollow proximal end of the penetrating member; however, if no fluid passage is desired, no guide tube or hub valve is required as shown in FIGS. 19 through 25. If a guide for the penetrating member is desired, a channel as shown in FIG. 20 or a rod as shown in FIGS. 23, 24 and 25 can be used.

The locking and releasing mechanism chosen for the automatic retractable safety penetrating instruments will depend upon ease of manufacture and assembly, holding or locking forces required and releasing forces required. The spacing of the trigger from the operating member during tissue penetration will determine the distal movement required of the operating member prior to automatic retraction. The configuration of the trigger will depend on the bias force on the operating member and the amount of movement required of the locking member to release the retraction member. The use of one piece, metal-or plastic strips or leaf springs to form the locking and releasing mechanisms facilitates assembly while assembly of multi-part locking and releasing mechanisms can be facilitated by use of a case to produce a module for installation in a hub as shown in FIGS. 11 and 12. In FIGS. 11, 13, 14 and 23, the retracting member also forms a stop to limit proximal movement of the penetrating member to assure alignment of the penetrating member and portal sleeve distal ends.

With the penetrating member carrying the operating member, automatic retractable safety penetrating instruments of the present invention have the appearance and tissue penetrating profile of standard trocar penetrating instruments; while, with the operating member carried by a probe movable within or externally of the penetrating member, entry into an anatomical cavity can be minimized while still having a configuration similar to a standard trocar penetrating instrument.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. An automatic retractable safety penetrating instrument for forming a portal communicating with an anatomical cavity for introduction of instruments therethrough comprising
   a portal sleeve having a distal end, a proximal end and a lumen extending between said sleeve distal and proximal ends;
   a penetrating member having a sharp distal end for penetrating tissue and being slidably disposed in said sleeve lumen;
   retracting means for moving said penetrating member from an extended position wherein said penetrating member distal end protrudes beyond said sleeve distal end to a retracted position wherein said penetrating member distal end is disposed within said sleeve lumen;

said penetrating member having an operative position between said retracted and extended positions wherein said penetrating member distal end is aligned with said portal sleeve distal end;

operating means movable distally with said penetrating member between said operative position and said extended position when said sleeve distal end enters an anatomical cavity; and trigger means for automatically actuating said retracting means in response to distal movement of said operating means to move said penetrating member to said retracted position whereby said penetrating member distal end is automatically retracted within said sleeve lumen when said sleeve distal end enters an anatomical cavity.

2. An automatic retractable safety penetrating instrument for forming a portal communicating with an anatomical cavity for introduction of instruments therethrough comprising a portal sleeve having a distal end, a proximal end and a lumen extending along a longitudinal axis between said sleeve distal and proximal ends;

a penetrating member having a proximal end, a sharp distal end for penetrating tissue and being slidably disposed in said sleeve lumen;

retracting means for moving said penetrating member from an extended position wherein said penetrating member distal end protrudes beyond said sleeve distal end to a retracted position wherein said penetrating member distal end is disposed within said sleeve lumen;

operating means movable distally when said sleeve distal end enters an anatomical cavity;

trigger means for automatically actuating said retracting means in response to distal movement of said operating means to move said penetrating member to said retracted position whereby said penetrating member distal end is automatically retracted within said sleeve lumen when said sleeve distal end enters an anatomical cavity; and a hub receiving said penetrating member proximal end and having slot means therein and pin means carried by said penetrating member proximal end and extending through said slot means transversely to said longitudinal axis to an end disposed externally of said hub to permit said pin means to be longitudinally manually moved to move said penetrating member.

3. An automatic retractable safety penetrating instrument for forming a portal communicating with an anatomical cavity for introduction of instruments therethrough comprising a portal sleeve having a distal end, a proximal end and a lumen extending between said sleeve distal and proximal ends;

a penetrating member having a sharp distal end for penetrating tissue and being slidably disposed in said sleeve lumen;

retracting means for moving said penetrating member from an extended position wherein said penetrating member distal end protrudes beyond said sleeve distal end to a retracted position wherein said penetrating member distal end is disposed within said sleeve lumen;

operating means movable distally when said sleeve distal end entering an anatomical cavity;

trigger means for automatically actuating said retracting means in response to distal movement of said operating means to move said penetrating member to said retracted position whereby said penetrating member distal end is automatically retracted within said sleeve lumen when said sleeve distal end enters an anatomical cavity; and a housing receiving said portal sleeve proximal end and a valve assembly disposed in said housing including an annular valve seat and a valve member biased to a closed position engaging said valve seat and movable to an open position against said bias, said valve assembly accommodating passage of said penetrating member therethrough and said valve seat and said valve member being integrally, unitarily formed of a resilient material.

4. An automatic retractable safety penetrating instrument for forming a portal communicating with an anatomical cavity for introduction of instruments therethrough comprising a portal sleeve having a distal end, a proximal end and a lumen extending between said sleeve distal and proximal ends;

a penetrating member having a sharp distal end for penetrating tissue and being slidably disposed in said sleeve lumen;

retracting means for moving said penetrating member from an extended position wherein said penetrating member distal end protrudes beyond said sleeve distal end to a retracted position wherein said penetrating member distal end is disposed within said sleeve lumen;

operating means movable distally along a longitudinal path when said sleeve distal end entering an anatomical cavity; and trigger means for automatically actuating said retracting means in response to distal movement of said operating means to move said penetrating member to said retracted position whereby said penetrating member distal end is automatically retracted within said sleeve lumen when said sleeve distal end enters an anatomical cavity, said trigger means includes a locking member for engaging said retracting means to prevent movement of said penetrating member to said retracted position and a trigger member positioned in said longitudinal path to be contacted by said operating means during distal movement thereof to move said locking member out of engagement with said retracting means.

5. An automatic retractable safety penetrating instrument as recited in claim 1 wherein said portal sleeve and said penetrating member have a common longitudinal axis, said retracting means includes a retracting spring biasing said penetrating member proximally and said operating means includes an operating member and an operating spring biasing said operating member distally.

6. An automatic retractable safety penetrating instrument as recited in claim 5 wherein said operating spring is disposed coaxially with said longitudinal axis.

7. An automatic retractable safety penetrating instrument as recited in claim 6 wherein said retracting spring is offset from said longitudinal axis.

8. An automatic retractable safety penetrating instrument as recited in claim 6 wherein said retracting spring is disposed coaxially with said longitudinal axis.

9. An automatic retractable safety penetrating instrument as recited in claim 8 wherein said retracting spring is disposed within said operating spring.

10. An automatic retractable safety penetrating instrument as recited in claim 5 wherein said operating spring is offset from said longitudinal axis.

11. An automatic retractable safety penetrating instrument as recited in claim 5 wherein said retracting spring and said operating spring have biased states in tension.

12. An automatic retractable safety penetrating instrument as recited in claim 5 wherein said retracting spring has a biased state in tension and said operating spring has a biased state in compression.

13. An automatic retractable safety penetrating instrument as recited in claim 5 wherein said retracting spring has a biased state in compression and said operating spring has a biased state in tension.

14. An automatic retractable safety penetrating instrument as recited in claim 5 wherein said operating spring and said retracting spring are coiled metal springs.

15. An automatic retractable safety penetrating instrument as recited in claim 5 wherein said operating spring is made of an elastic material.

16. An automatic retractable safety penetrating instrument as recited in claim 5 wherein said retracting spring is made of an elastic material.

17. An automatic retractable safety penetrating instrument as recited in claim 5 wherein said operating spring is made from a metal strip.

18. An automatic retractable safety penetrating instrument as recited in claim 5 wherein said retracting spring is made from a metal strip.

19. An automatic retractable safety penetrating instrument as recited in claim 5 wherein said operating spring and said retracting spring are integrally, unitarily made from a single metal strip.

20. An automatic retractable safety penetrating instrument as recited in claim 19 wherein said trigger means is made from said single metal strip.

21. An automatic retractable safety penetrating instrument as recited in claim 5 wherein said retracting spring is disposed within said penetrating member.

22. An automatic retractable safety penetrating instrument as recited in claim 5 wherein said operating spring is disposed within said penetrating member.

23. An automatic retractable safety penetrating instrument as recited in claim 5 wherein said operating spring and said retracting spring are disposed within said penetrating member.

24. An automatic retractable safety penetrating instrument as recited in claim 5 wherein said operating spring and said retracting spring are in unbiased states when said penetrating member is in said retracted position.

25. An automatic retractable safety penetrating instrument as recited in claim 24 wherein said operating spring and said retracting spring are in biased states when said penetrating member is in said extended position.

26. An automatic retractable safety penetrating instrument as recited in claim 1 and further comprising means for manually moving said penetrating member from said retracted position to said extended position.

27. An automatic retractable safety penetrating instrument as recited in claim 1 wherein said operating means includes an operating spring biasing said penetrating member distally and said retraction means includes abutment means for limiting proximal movement of said penetrating member against said operating spring to said operative position, said abutment means being movable with actuation of said retraction means to permit movement of said penetrating member to said retracted position.

28. An automatic retractable safety penetrating instrument as recited in claim 27 and further comprising means for manually moving said penetrating member from said extended position to said operative position.

29. An automatic retractable safety penetrating instrument as recited in claim 28 wherein said manual moving means allows manual movement of said penetrating member from said retracted position to said extended position.

30. An automatic retractable safety penetrating instrument as recited in claim 27 and further comprising means for manually moving said penetrating member from said retracted position to said operative position.

31. An automatic retractable safety penetrating instrument as recited in claim 2 wherein said slot means includes a longitudinal portion permitting longitudinal movement of said pin means between said retracted and extended positions.

32. An automatic retractable safety penetrating instrument as recited in claim 31 wherein said slot means includes a transverse slot portion for receiving said pin means to hold said penetrating member in said retracted position.

33. An automatic retractable safety penetrating instrument as recited in claim 31 wherein said slot means includes a transverse slot portion for receiving said pin means to hold said penetrating member in said extended position.

34. An automatic retractable safety penetrating instrument as recited in claim 33 wherein said slot means includes a second transverse slot portion for receiving said pin means to hold said penetrating member in said retracted position.

35. An automatic retractable safety penetrating instrument as recited in claim 3 wherein said annular valve seat is disposed at a distal end of a body having a passage therethrough and a flange extending therefrom, said valve seat, valve member, body and flange being integrally, unitarily formed of said resilient material.

36. An automatic retractable safety penetrating instrument as recited in claim 35 wherein said valve assembly is removably mounted in said housing to permit valve assemblies with varying size body passages to be interchangeably mounted in said housing to accommodate instruments of varying size in sealing engagement.

37. An automatic retractable safety penetrating instrument as recited in claim 4 wherein said locking member and said trigger member are integrally, unitarily made from a single metal strip.

38. An automatic retractable safety penetrating instrument as recited in claim 4 wherein said trigger member is pivotally mounted in a case, said locking member is mounted in said case and said penetrating member has a proximal end and further comprising a hub receiving said penetrating member proximal end, said case being mounted in said hub to position said locking member adjacent said retracting means and said trigger member adjacent said operating means.

39. An automatic retractable safety penetrating instrument as recited in claim 1 wherein said retracting means includes a retracting member coupled with said penetrating member and allowing limited proximal movement of said penetrating member.

40. An automatic retractable safety penetrating instrument as recited in claim 39 wherein said retracting member includes a retraction plate having an opening for receiving said penetrating member and an abutment member for engaging said penetrating member to limit proximal movement thereof.

41. An automatic retractable safety penetrating instrument as recited in claim 40 wherein said trigger means includes a locking member engaging said retraction plate to prevent proximal movement of said retracting member and a trigger member actuated by distal movement of said operating means to move said locking member out of engagement with said retraction plate and said retracting means includes spring means coupled with said retracting member for moving said penetrating member to said retracted position when said locking member moves out of engagement with said retraction plate.

42. An automatic retractable safety penetrating instrument as recited in claim 40 wherein said trigger means includes a locking member engaging said abutment member to prevent proximal movement of said retracting member and a trigger member disposed distally of said locking member to be actuated by distal movement of said operating means to move said locking member out of engagement with said abutment member and said retracting means includes spring means coupled with said retracting member for moving said penetrating member to said retracted position when said locking member moves out of engagement with said abutment member.

43. An automatic retractable safety penetrating instrument as recited in claim 1 wherein said operating means includes an operating member for actuating said trigger means, said operating member being carried by said penetrating member.

44. An automatic retractable safety penetrating instrument as recited in claim 43 wherein said trigger means includes a trigger member positioned to be engaged by said operating member, said penetrating member distal end is distally spaced from said portal sleeve distal end in said extended position, said penetrating member distal end aligned with said portal sleeve distal end in said operative position, said operating member being disposed distally of said trigger member when said penetrating member is in said extended position and said operating member being disposed proximally of said trigger member when said penetrating member is in said operative position.

45. An automatic retractable safety penetrating instrument as recited in claim 44 and further comprising means for manually moving said penetrating member from said extended position to said operative position.

46. An automatic retractable safety penetrating instrument as recited in claim 44 and further comprising stop means disposed within said portal sleeve for abutment with said penetrating member to limit proximal movement of said penetrating member to said operative position to provide positive alignment of said penetrating member distal end with said portal sleeve distal end.

47. An automatic retractable safety penetrating instrument as recited in claim 44 and further comprising means for selectively holding said penetrating member in said operative position to prevent retraction of said penetrating member.

48. An automatic retractable safety penetrating instrument as recited in claim 44 wherein said penetrating member has a proximal end and further comprising a hub receiving said penetrating member proximal end and stop means disposed within said hub for abutment with said penetrating member proximal end to limit proximal movement of said penetrating member to said operative position to provide positive alignment of said penetrating member distal end with said portal sleeve distal end.

49. An automatic retractable safety penetrating instrument as recited in claim 1 wherein said penetrating member has a proximal end and further comprising a hub receiving said penetrating member proximal end and including guide means for guiding retracting movement of said penetrating member.

50. An automatic retractable safety penetrating instrument as recited in claim 49 wherein said penetrating member proximal end has a channel therein and said guide means includes a rod received in said channel.

51. An automatic retractable safety penetrating instrument as recited in claim 49 wherein said penetrating member proximal end is hollow and said guide means includes a tube received in said penetrating member proximal end.

52. An automatic retractable safety penetrating instrument as recited in claim 51 wherein said penetrating member includes a passage from said penetrating member distal end to said hollow penetrating member proximal end and said hub includes a valve communicating with said guide tube.

53. An automatic retractable safety penetrating instrument as recited in claim 1 wherein said portal sleeve has a first configuration when said penetrating member is in said extended position and automatically assumes a second configuration when said penetrating member is moved to said retracted position.

54. An automatic retractable safety penetrating instrument as recited in claim 53 wherein said second configuration is curved.

55. An automatic retractable safety penetrating instrument as recited in claim 54 wherein said second configuration is "J" shaped.

56. An automatic retractable safety penetrating instrument as recited in claim 1 wherein said portal sleeve has a longitudinal axis, said portal sleeve includes a portion distal of said penetrating member distal end when said penetrating member is in said retracted state and said portal sleeve distal portion has a non-linear configuration to extend away from said axis.

* * * * *